(12) United States Patent
Kato et al.

(10) Patent No.: US 6,579,249 B2
(45) Date of Patent: Jun. 17, 2003

(54) OCCLUSAL FORCE MEASURING APPARATUS

(75) Inventors: Takahito Kato, Hamamatsu (JP); Tsunehiko Takeuchi, Hamamatsu (JP); Takehiro Kurono, Hamamatsu (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

(21) Appl. No.: 09/949,981

(22) Filed: Sep. 12, 2001

(65) Prior Publication Data

US 2002/0032392 A1 Mar. 14, 2002

(30) Foreign Application Priority Data

Sep. 11, 2000 (JP) ........................................ 2000-275082

(51) Int. Cl.[7] ........................... A61B 5/103; A61B 5/117
(52) U.S. Cl. .................................................... 600/590
(58) Field of Search ................................. 600/590, 310, 600/322; 356/39

(56) References Cited

U.S. PATENT DOCUMENTS 5,632,273 A 5/1997 Suzuki ........................ 128/633

FOREIGN PATENT DOCUMENTS

JP 7-255709 10/1995

*Primary Examiner*—Max F. Hindenburg
*Assistant Examiner*—Brian Szmal
(74) *Attorney, Agent, or Firm*—Morgan, Lewis & Bockius LLP (57) ABSTRACT

A light irradiating section irradiates a muscle used for occlusion of teeth, with light, and a light detecting section detects scattered light from the muscle. An oxygen saturation acquiring section acquires an oxygen saturation of the muscle, based on the scattered light thus detected. Further, based on correlation data between oxygen saturation and occlusal force stored in a correlation data storing section, an occlusal force calculating section calculates the occlusal force of the subject corresponding to the oxygen saturation acquired.

8 Claims, 10 Drawing Sheets

OCCLUSAL FORCE MEASURING APPARATUS

BACKGROUND OF THE INVENTION

1. Field of the Invention

The present invention relates to occlusal force measuring apparatus.

2. Related Background Art

The conventionally known apparatus for measuring the occlusal force being the bite force of the upper and lower teeth includes such a system that a pressure sensitive sheet is inserted into the oral cavity to be bitten and that occlusal traces recorded in the pressure sensitive sheet are read by a scanner to gain the occlusal force, and such a system that a compact pressure detector filled with liquid is inserted into the oral cavity to be bitten and that a pressure transmitted through the liquid is measured by a load cell located outside.

SUMMARY OF THE INVENTION

However, since the measuring system with the pressure sensitive sheet is configured to insert the pressure sensitive sheet into the oral cavity to make it bitten and thereafter analyze the pressure sensitive sheet in a post-step, it does not allow real-time measurement and can measure only the maximum occlusal force during occlusion. In the case of the measuring system with the compact pressure detector, this detector has to be bitten in the oral cavity and thus the system cannot measure the occlusal force in a natural state as if to chew food.

The present invention has been accomplished in view of the above problems and an object of the invention is to provide occlusal force measuring apparatus that can measure the occlusal force in real time without the necessity for biting any detector or the like at all.

An occlusal force measuring apparatus according to the present invention is an apparatus for measuring an occlusal force of a subject, which comprises a light irradiating section for irradiating a muscle used for occlusion of teeth of the subject, with light; a light detecting section for detecting scattered light from the muscle upon irradiation of the muscle with the light; an oxygen saturation acquiring section for acquiring an oxygen saturation, based on the scattered light; a correlation data storing section prestoring correlation data between oxygen saturation and occlusal force; and an occlusal force calculating section for calculating an occlusal force corresponding to the oxygen saturation acquired by the oxygen saturation acquiring section, based on the correlation data stored in the correlation data storing section.

According to the present invention, the light irradiating section irradiates the muscle used for the occlusion of teeth, with the light and the light detecting section detects the scattered light from the muscle; thus, the oxygen saturation of this muscle is acquired based on the scattered light. Further, the occlusal force of the subject is calculated based on the correlation between oxygen saturation and occlusal force.

In a preferred embodiment, a set of a light irradiating section and a light detecting section constitute a left scattered light acquiring section mountable on the left side of the subject's face, and another set of a light irradiating section and a light detecting section constitute a right scattered light acquiring section mountable on the right side of the subject's face. This configuration permits the apparatus to calculate left and right occlusal forces of the subject independently of each other.

The apparatus may be configured to comprise a left and right comparing section for comparing left and right occlusal forces calculated based on scattered light detected by the left scattered light acquiring section and the right scattered light acquiring section. This configuration permits the apparatus to compare the left and right occlusal forces of the subject with each other.

The apparatus may also be configured so that the correlation data storing section stores correlation data between oxygen saturation and occlusal force for every subject and the occlusal force calculating section calculates the occlusal force, based on the correlation data for every subject. In this configuration, the occlusal force calculating section calculates the occlusal force, based on the correlation data between oxygen saturation and occlusal force for every subject.

The apparatus may also be configured to comprise a reference occlusal force storing section storing a reference occlusal force and a clenching situation acquiring section for acquiring the number of times that the calculated occlusal force becomes not less than the reference occlusal force, hours when the calculated occlusal force becomes not less than the reference occlusal force, and occlusal forces at the hours. This configuration permits the apparatus to acquire clenching situations of the subject with variation in time.

The apparatus may also be configured to comprise a reference occlusal force storing section storing a reference occlusal force and a ratio calculating section for calculating a ratio of the calculated occlusal force to the reference occlusal force. This configuration permits the apparatus to calculate the ratio of the current occlusal force to the reference occlusal force.

The apparatus may also be configured to comprise a standard mastication storing section storing a time variation of occlusal force during chewing of a predetermined food, and a mastication comparing section for comparing the time variation of occlusal force during the chewing of the predetermined food with a time variation of the calculated occlusal force. This configuration permits the apparatus to compare the time variation of occlusal force during the subject's mastication of the food with standard values.

The apparatus may also be configured to comprise an individual occlusal force storing section storing the calculated occlusal force for every subject, and an occlusal force comparing section for comparing the calculated occlusal force with the occlusal force of each subject stored. This configuration permits the apparatus to compare the current occlusal force of the subject with the occlusal force measured in the past.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

The present invention may be more readily described with reference to the accompanying drawings, in which.

DESCRIPTION OF THE PREFERRED EMBODIMENTS

The preferred embodiments of the occlusal force measuring apparatus according to the present invention will be described hereinafter in detail with reference to the accompanying drawings. Throughout the description of the drawings, identical or equivalent elements will be denoted by the same reference symbols and redundant description will be omitted.

Figure 1:
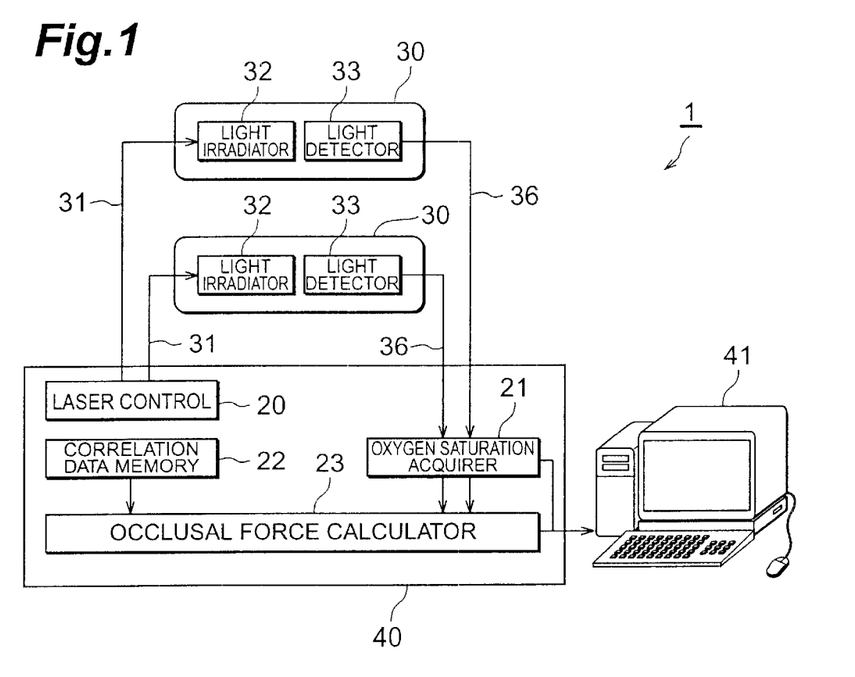
FIG. 1 is a block diagram of the occlusal force measuring apparatus in the first embodiment and the second embodiment.

In the first place, the occlusal force measuring apparatus 1 of the first embodiment will be described referring to FIG. 1. This apparatus 1 is an apparatus configured to irradiate the muscle (masseter) used for occlusion of teeth of a subject, with laser light, detect scattered light from the masseter to measure an oxygen saturation, and calculate the occlusal force, based on this oxygen saturation, and is provided with two probes 30, 30 for irradiating the subject's masseters with the laser light and receiving scattered light, a main body 40 for outputting the laser light and calculating occlusal forces, and a display 41 for displaying data of resultant occlusal forces or the like.

The main body 40 incorporates a laser control section 20 for generating pulsed laser light, an oxygen saturation acquiring section 21 for acquiring an oxygen saturation in the blood of each masseter based on intensity of scattered light from the masseter, a correlation data storing section 22 prestoring the correlation data between oxygen saturation and occlusal force, and an occlusal force calculating section 23 for calculating the occlusal forces of the subject, based on the obtained oxygen saturations.

The laser control section 20 has a semiconductor laser device and can emit the pulsed laser light in the near infrared region. The laser light outputted from this laser control section 20 is transmitted through an optical fiber 31 to a light irradiating section 32 of each probe 30.

Figure 2:
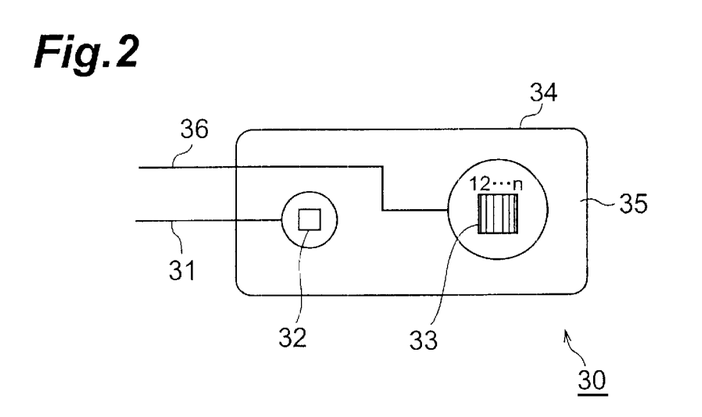
FIG. 2 is a schematic view showing a probe of FIG. 1.

The probe 30, as shown in FIG. 2, is provided with the foregoing light irradiating section 32 for irradiating the masseter with the laser light, a light detecting section 33 for detecting the scattered light from the masseter upon the irradiation, and a platelike holder 34 for holding these sections. The holder 34 is flexible silicone rubber, and the light irradiating section 32 and the light detecting section 33 are spaced several cm (4 cm in the present embodiment) apart from each other on the surface of the holder 34. The holder 34 can be stuck through pressure sensitive adhesive tape 35 to the skin. The light irradiating section 32 is comprised of a prism and the laser light transmitted through the optical fiber 31 emerges normally from the exit surface of the light irradiating section 32. The light detecting section 33 consists of an array of n photodiodes and the photodiodes are juxtaposed in the same direction as the arranging direction of the light irradiating section 32 and the light detecting section 33. This permits the detecting section to measure the intensity of scattered light at each of n points different in the distance from the light irradiating section 32. This light detecting section 33 may also be a two-dimensional photosensor in which photodiodes are arranged two-dimensionally, and the photodiodes can be replaced with charge coupled devices (CCDs). Signals of scattered light detected by the light detecting section 33 are sent through a cable 36 to the oxygen saturation acquiring section 21.

The oxygen saturation acquiring section 21 acquires the oxygen saturation in blood, based on a change rate of the intensity of scattered light detected by the light detecting section 33, against the distance from the light irradiating section 32, and it is described in detail, for example, in Japanese Patent Application Laid-Open No. H07-255709 and U.S. Pat. No. 5,632,273. In brief, the concentration measuring device disclosed in this application is configured to calculate a change rate of detected light quantity (optical density OD) against distance from a light incidence point and calculate a relative concentration ratio of a measured component, based on a predetermined relation between the resultant change rate of detected light quantity and light absorption coefficient $\mu a$.

Figure 3:
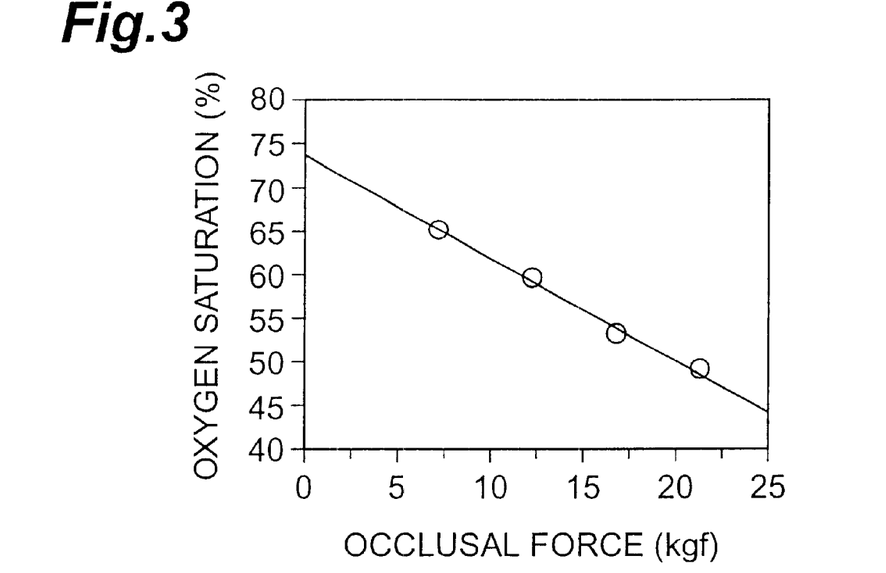
FIG. 3 is a graph showing a correlation between occlusal forces measured by the method of inserting the detector into the oral cavity, and oxygen saturations of the masseter.
Figure 4:
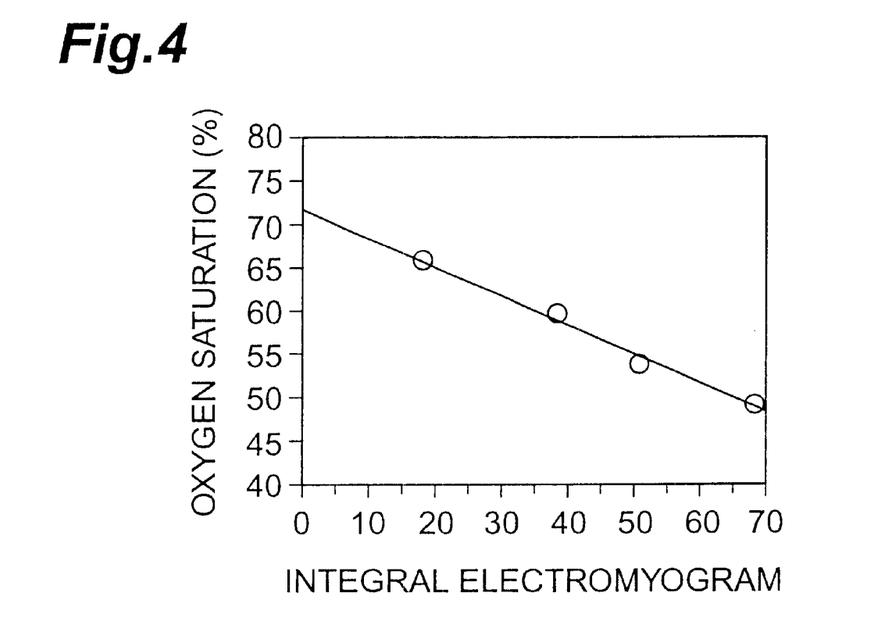
FIG. 4 is a graph showing a correlation between electromyogram of the masseter and oxygen saturations of the masseter.
Figure 5:
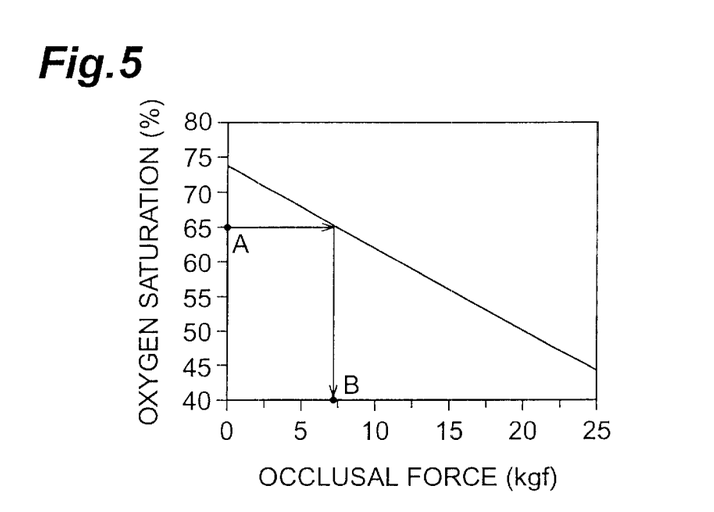
FIG. 5 is a graph showing correlation data between oxygen saturations prestored in the correlation data storing section of FIG. 1, and occlusal forces.

The correlation data storing section 22 prestores the correlation data for calculation of occlusal force from the oxygen saturation acquired by the oxygen saturation acquiring section 21, and the occlusal force calculating section 23 has a function of calculating an occlusal force from an oxygen saturation, using this correlation data. FIG. 3 is a graph showing a relation between oxygen saturations of the masseter of a certain subject and occlusal forces measured by an occlusal force gauge of the conventional type in which the compact detector is inserted into the oral cavity, and FIG. 4 a graph showing a relation between oxygen saturations of the masseter and electromyogram of the masseter. As apparent from FIG. 3 and FIG. 4, there is a correlation between oxygen saturation and occlusal force. It is thus possible to calculate an occlusal force corresponding to an oxygen saturation if data of the relation between oxygen saturation and occlusal force is preliminarily acquired for many subjects and if an average of the data is stored as correlation data in the correlation data storing section 22. In the present embodiment, the correlation data as shown in FIG. 5 is prestored in the correlation data storing section 22.

Figure 6:
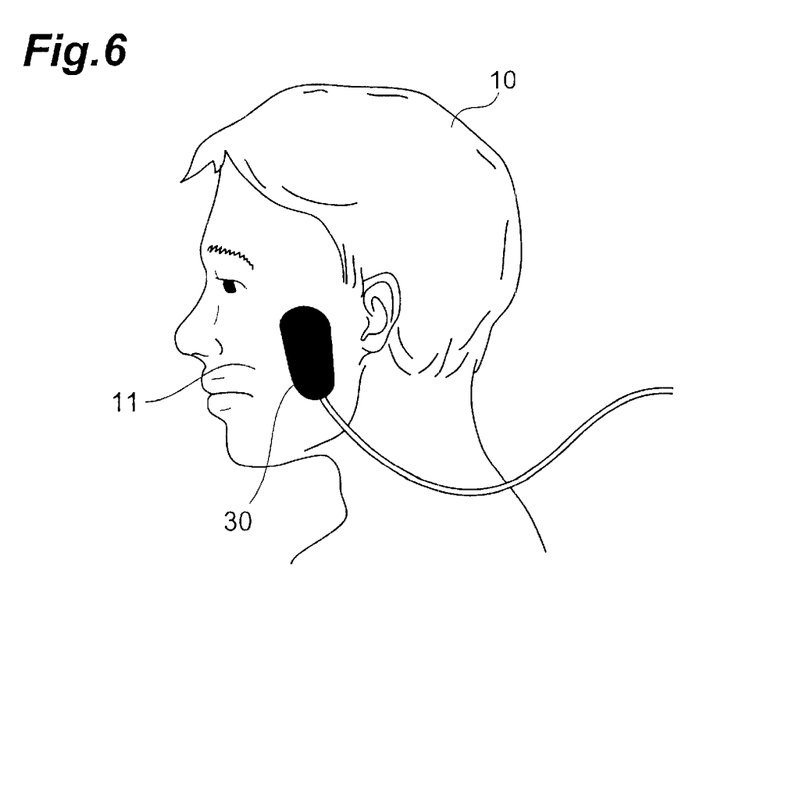
FIG. 6 is an explanatory diagram showing a method of sticking the probe of FIG. 1 to a subject.
Figure 7:
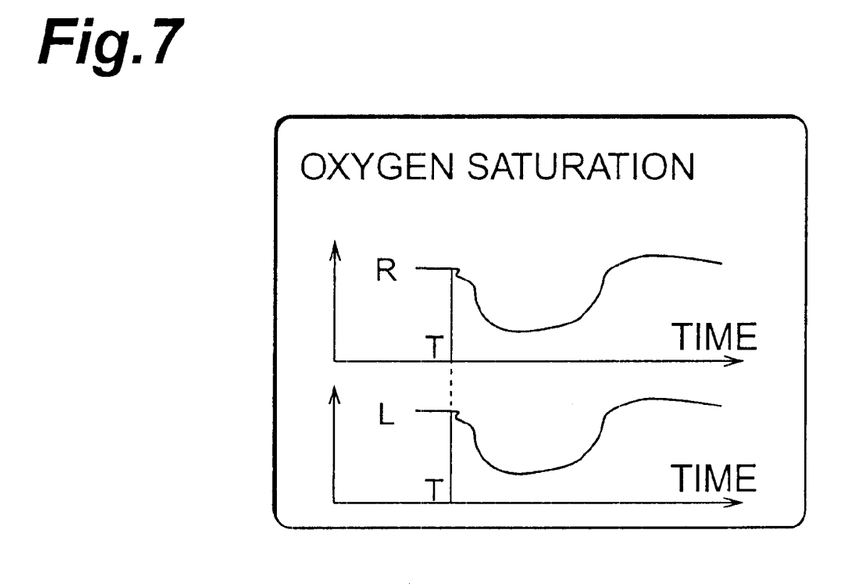
FIG. 7 is a diagram showing an example of oxygen saturations displayed on a display device of FIG. 1.

The procedures of the measurement by the occlusal force measuring apparatus 1 of the present embodiment will be described below. First, the probes 30 are stuck to the skin right above the left and right masseters of subject 10, as shown in FIG. 6. Then the pulsed laser light generated by the laser control section 20 shown in FIG. 1 is guided through the optical fibers 31 to be outputted from the respective light irradiating sections 32 of the left and right probes 30, whereby the left and right masseters are irradiated through the skin with the light. The light propagates in the masseters to be scattered, and the scattered light is detected by each of the left and right light detecting sections 33 to yield intensity data of scattered light at the n points of the different distances from the incident point for each of the left and right masseters. Next, the oxygen saturation acquiring section 21 acquires each of oxygen saturations in blood of the left and right masseters from the intensity data of scattered light at the n points. Then the oxygen saturations obtained are displayed on the display 41 as occasion demands. FIG. 7 is a diagram showing an example of time variation of oxygen saturations displayed on the display 41, in which clenching of teeth is started from a time T (T in FIG. 7).

Figure 8:
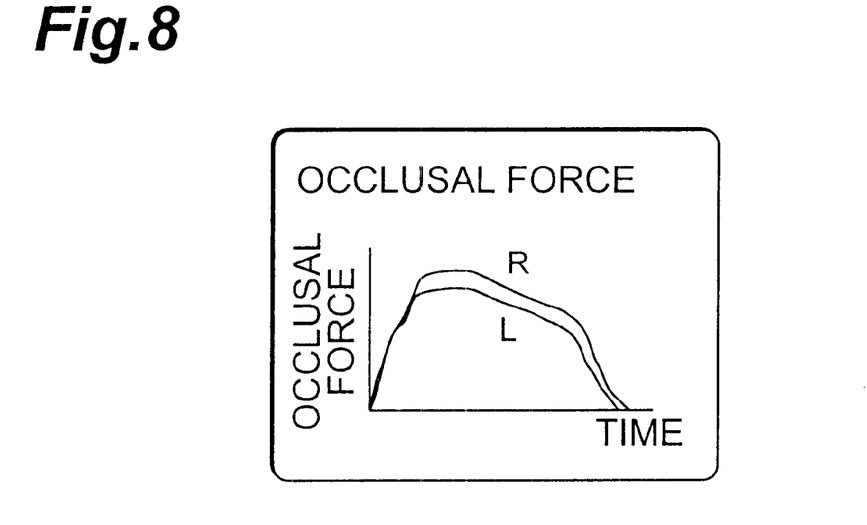
FIG. 8 is a diagram showing an example of left and right occlusal forces displayed on the display device of FIG. 1.

In the next place, the occlusal force calculating section 23 calculates the left and right occlusal forces of the subject 10 corresponding to the resultant oxygen saturations, based on the correlation data stored in the correlation data storing section 22. For example, where the oxygen saturation of the subject 10 is 65%, as shown in FIG. 5, the occlusal force of 7 kgf (B in FIG. 5) is calculated as an occlusal force corresponding to the oxygen saturation of 65% (A in FIG. 5). This processing from the detection of the laser light to the calculation of occlusal force is repeatedly carried out every output of the pulsed laser light, so as to measure occlusal forces in real time. Then the left and right occlusal forces obtained in this way are displayed on the display 41. An example of the occlusal forces displayed is presented in FIG. 8.

In the occlusal force measuring apparatus 1 of the present embodiment, as described above, the probes 30 are stuck through the pressure sensitive adhesive tape 35 to the skin to measure the oxygen saturations of the masseters under irradiation with the light from the outside and the occlusal forces corresponding to the oxygen saturations are calculated based on the correlation data; therefore, it becomes feasible to measure the occlusal forces in real time without the necessity for biting any detector or the like at all. Since the apparatus is provided with the two probes 30, each consisting of the light irradiating section 32 and the light detecting section 33 and being stuck to the skin 11 right above the left or right masseter of the subject 10, the left and right occlusal forces of the subject 10 can be calculated independently of each other.

Figure 9:
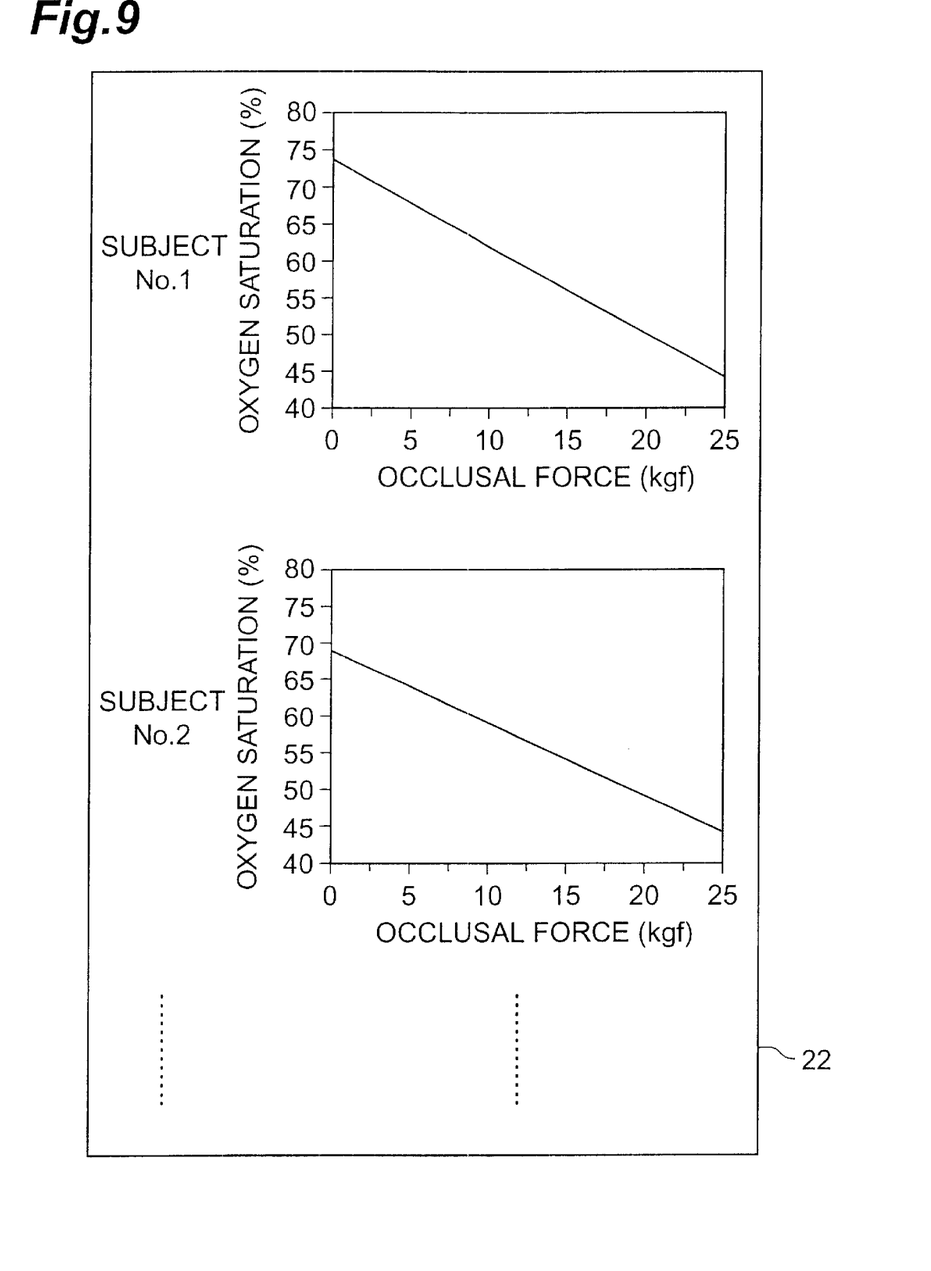
FIG. 9 is a diagram showing correlation data between oxygen saturation and occlusal force for every subject, prestored in the correlation data storing section of FIG. 1.

The second embodiment will be described next. The occlusal force measuring apparatus 1 of the present embodiment is constructed in such structure that the correlation data storing section 22 of the occlusal force measuring apparatus 1 of the first embodiment is modified to be able to store the correlation data between occlusal force and oxygen saturation for every subject 10 (see FIG. 9) and that the occlusal force calculating section 23 calculates an occlusal force corresponding to an oxygen saturation, based on the correlation data for each subject 10, instead of the average correlation data of the first embodiment.

The procedures of the measurement of the occlusal force measuring apparatus 1 of the present embodiment are as follows. First, the relation between oxygen saturation and occlusal force is measured for every subject 10 by the conventional occlusal force gauge or the like and the data obtained is stored as correlation data between occlusal force and oxygen saturation intrinsic to each subject 10 in the correlation data storing section 22 for every subject 10. Then the oxygen saturations of the masseters are acquired according to the procedures similar to those in the first embodiment and occlusal forces are calculated from the oxygen saturations obtained, based on the correlation data for each of individuals stored in the correlation data storing section 22, and are displayed on the display 41.

Since the occlusal forces are calculated from the oxygen saturations, based on the correlation data for every individual as described above, this eliminates errors due to individual differences that can occur in use of the average correlation, so that the occlusal forces can be calculated with high accuracy for each of individuals.

Figure 10:
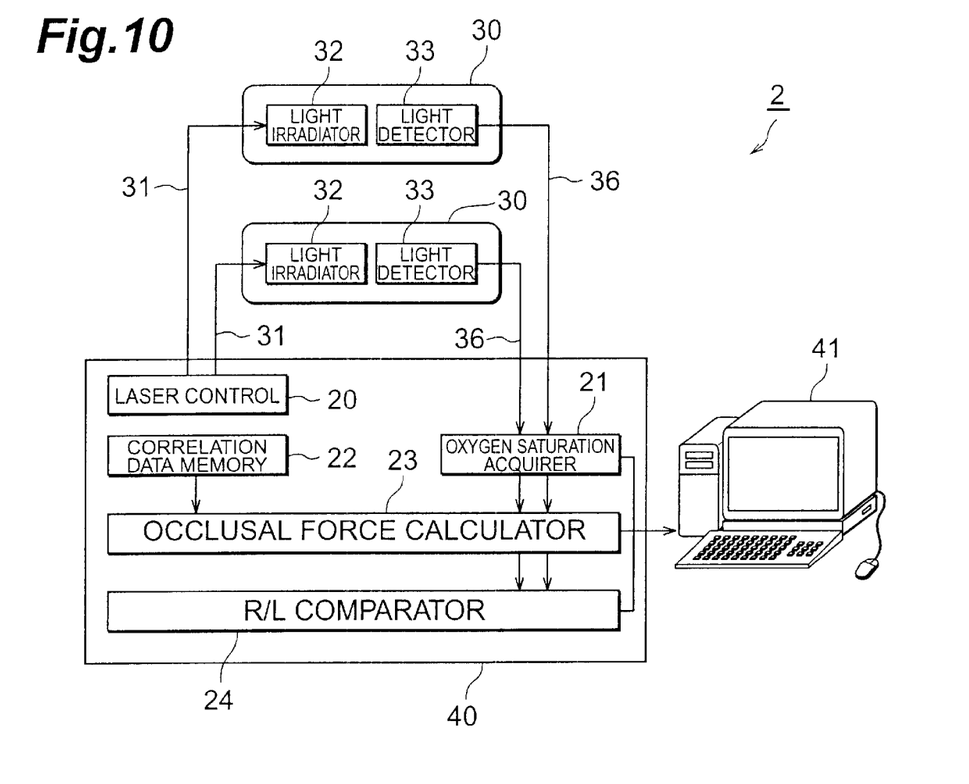
FIG. 10 is a block diagram of the occlusal force measuring apparatus of the third embodiment.

In the next place, the third embodiment will be described with reference to FIG. 10. The occlusal force measuring apparatus 2 of the present embodiment is equipped with a left and right comparing section 24 for comparing the left and right occlusal forces with each other, in addition to the structure of the occlusal force measuring apparatus 1 of the second embodiment, as shown in FIG. 10, and the display 41 displays the result of the comparison. The left and right comparing section 24 compares the left and right occlusal forces calculated, with each other and calculates the difference between the left and right occlusal forces.

Figure 11:
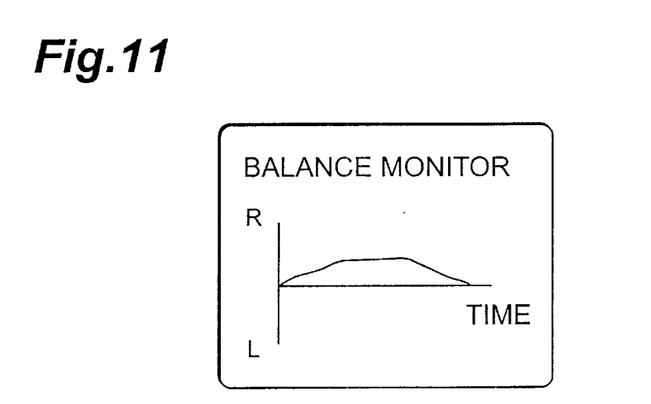
FIG. 11 is a diagram showing an example of the difference between the left and right occlusal forces, displayed on the display device of FIG. 9.

The measurement procedures of the occlusal force measuring apparatus 2 of the present embodiment are as follows. First, the measurement is carried out according to the procedures similar to those in the second embodiment to calculate the left and right occlusal forces. Next, the left and right comparing section 24 compares the left and right occlusal forces to display the difference between the left and right occlusal forces on the display 41 (see FIG. 11). Then a subject 10 with a poor occlusion balance between the left and right forces is subjected to correction and training for chewing, while checking the difference between the left and right occlusal forces.

Since the apparatus is provided with the left and right comparing section 24 for comparing the left and right occlusal forces and is arranged to perform the evaluation of the balance between the left and right occlusal forces in real time as described above, it is feasible to make the evaluation and correction for the balance between the left and right occlusal forces of the subject 10. Although in the present embodiment the left and right comparing section 24 calculates the difference between the left and right occlusal forces, the apparatus may be modified so as to acquire evaluation labels to classify the occlusal forces stepwise like A, B, and C, based on preset ranges of occlusal forces; or, so as to calculate an average of the left and right occlusal forces, calculate deviations of the left and right occlusal forces therefrom, and acquire values obtained by dividing the deviations by the average, or the like.

Figure 12:
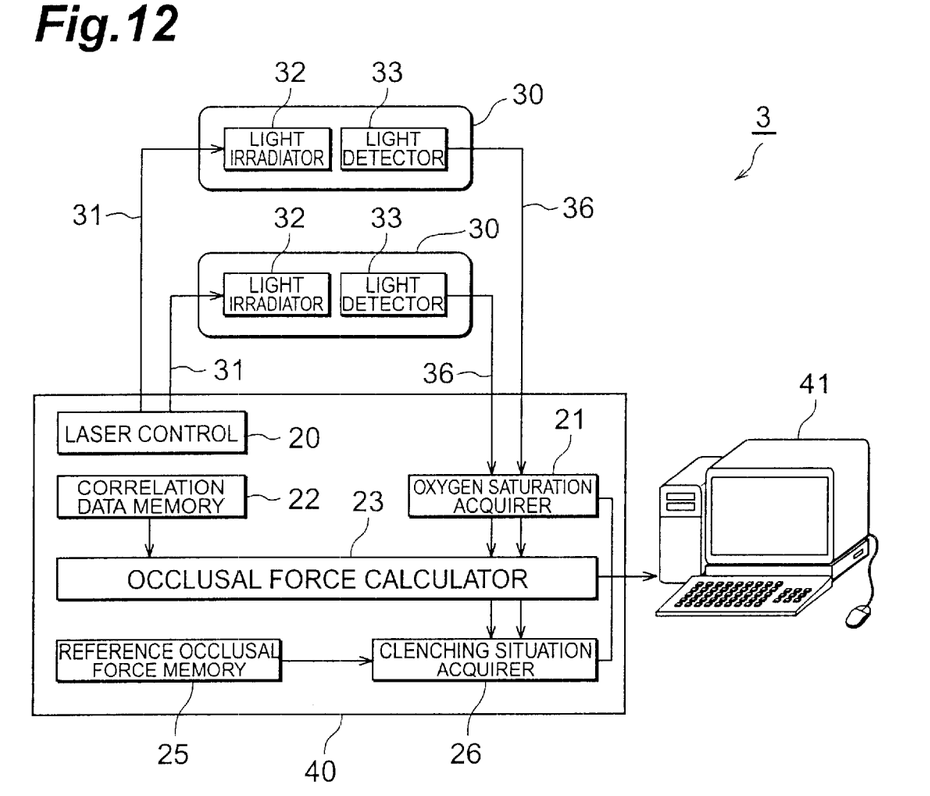
FIG. 12 is a block diagram of the occlusal force measuring apparatus of the fourth embodiment.

The fourth embodiment will be described below referring to FIG. 12. The occlusal force measuring apparatus 3 of the present embodiment is provided with a reference occlusal force storing section 25 storing a reference occlusal force and a clenching situation acquiring section 26 for acquiring the number of times that the occlusal force is not less than the reference occlusal force, hours when it occurs, and occlusal forces at the hours, in addition to the structure of the occlusal force measuring apparatus 1 of the second embodiment, as shown in FIG. 12, and the display 41 displays the clenching situation acquired.

The measurement procedures of the occlusal force measuring apparatus 3 of the present embodiment are as follows. First, a threshold occlusal force judged as clenching is set as a reference occlusal force in the reference occlusal force storing section 25. Then occlusal forces of a subject 10 in sleep are continuously acquired according to the procedures similar to those in the second embodiment, and the clenching situation acquiring section 26 acquires hours when the occlusal force is greater than the reference occlusal force, the number of times that it occurs, occlusal forces at the hours, and so on. Then this clenching state data is displayed on the display 41 and the data about the clenching during sleep, the number and frequency of bruxisms, and so on is used as basic data for occlusion therapy.

Since the apparatus is configured to set the reference occlusal force in the reference occlusal force storing section 25, acquire hours of measurements of occlusal forces over the reference occlusal force, the number of times thereof, and occlusal forces at the hours in the clenching situation acquiring section 26, and thereby acquire the clenching situation of the subject 10 with a lapse of time as described above, it becomes feasible to provide the occlusal therapy while keeping track of the situation of clenching, bruxism, etc. of the subject 10.

Figure 13:
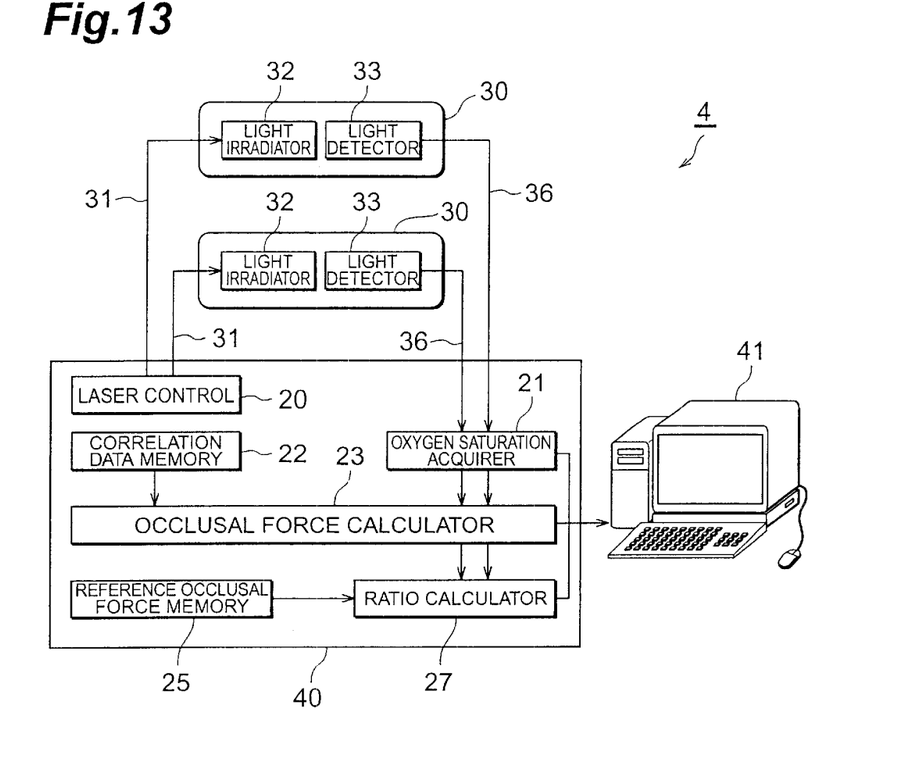
FIG. 13 is a block diagram of the occlusal force measuring apparatus of the fifth embodiment.

The fifth embodiment will be described below with reference to FIG. 13. The occlusal force measuring apparatus 4 of the present embodiment is provided with a ratio calculating section 27 for calculating a ratio of a current occlusal force to the reference occlusal force set in the reference occlusal force storing section 25 instead of the clenching situation acquiring section in the occlusal force measuring apparatus 3 of the fourth embodiment, as shown in FIG. 13, and the display 41 displays the ratio.

The measurement procedures of the occlusal force measuring apparatus 4 of the present embodiment will be described. As an example thereof, here is described a use method where the reference occlusal force is the maximum occlusal force of the subject 10. As the ratio to the maximum occlusal force of the subject 10 is calculated, it becomes feasible for the subject 10 to impose occlusal forces at a certain ratio to the maximum occlusal force. This is useful in such occlusion therapy that the subject is made to bite a pressure sensitive sheet, which demonstrates changes in color depending upon pressures, at a desired occlusal force to obtain occlusal traces and they are analyzed.

First, the subject 10 is made to clench the teeth at the maximum, the occlusal forces at that time are calculated according to the procedures similar to those in the fourth embodiment, and the maximum occlusal force at this time is set as a reference occlusal force in the reference occlusal force storing section 25. Then the pressure sensitive sheet is inserted into the oral cavity of the subject 10 and the subject is made to lightly bite this sheet. At this time, the ratio of the occlusal force to the reference occlusal force is calculated in the ratio calculating section 27 and displayed on the display 41. Viewing it, the subject 10 adjusts the ratio of the occlusal force to the maximum occlusal force to 30%, thereby acquiring the pressure sensitive sheet with occlusal traces thereon at the occlusal force of 30%. Likewise, other pressure sensitive sheets are also acquired at respective occlusal forces of 50%, 70%, and 100% and the occlusal traces of these pressure sensitive sheets are used to yield contact areas and occlusal pressures in occlusion of the upper and lower teeth at each of the occlusal forces, which are utilized as the basic data for occlusal therapy.

Since the apparatus is provided with the reference occlusal force storing section 25 and the ratio calculating section 27 and configured to calculate and display the ratio of the current occlusal force to the maximum occlusal force of the subject 10 as described above, it becomes feasible to let the subject 10 occlude at a desired force. This reference occlusal force does not always have to be limited to only the maximum of measured occlusal forces, but it can also be, for example, an average of occlusal forces of male adults or the like.

Figure 14:
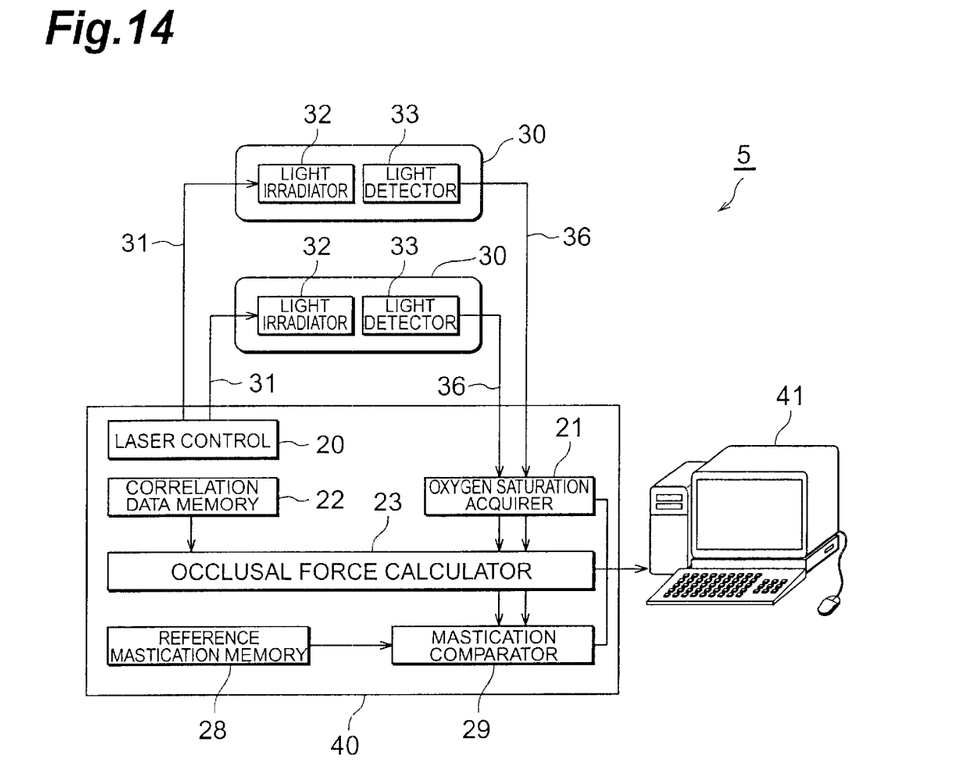
FIG. 14 is a block diagram of the occlusal force measuring apparatus of the sixth embodiment.

The sixth embodiment will be described below with reference to FIG. 14. The occlusal force measuring apparatus 5 of the present embodiment is provided with a standard mastication storing section 28 for storing a time variation of occlusal force during chewing of a predetermined food and a mastication comparing section 29 for comparing the time variation of occlusal force during chewing of the predetermined food with a calculated time variation of occlusal force, in addition to the structure of the occlusal force measuring apparatus 1 of the second embodiment, as shown in FIG. 14, and the display 41 displays the result of this evaluation.

The measurement procedures of the occlusal force measuring apparatus 5 of the present embodiment will be described. Constructed in the first place is a database about time variations of occlusal force during chewing of various foods. The first step is preliminarily to let the subject masticate a food of a fixed size (an apple or the like) and acquire a time variation of occlusal force according to the procedures similar to those in the second embodiment. This step is repeated with many foods and many subjects and a mean temporal variation of occlusal force is calculated for every food. The results are stored as a database of standard time variations of occlusal force in the standard mastication storing section 28 for every food. The database herein is classified by only the foods, but the classification can also be made in consideration of such factors as ages, presence/absence of dental caries, and so on in addition to the foods.

In the next place, a habit or the like of mastication of a specific subject 10 is captured based on this database. First, the specific subject 10 is given a food of a certain size and made to masticate it, thereby acquiring a time variation of occlusal force in the same manner as before. Then the mastication comparing section 29 compares the time variation of occlusal force thus acquired, with the standard time variation of occlusal force corresponding to that food, stored in the standard mastication storing section 28, and the result of this comparison is displayed on the display 41. Then the mastication way of the subject 10 is corrected while viewing this result.

Since the apparatus is provided with the standard mastication storing section 28 and configured to compare the time variation of occlusal force of the subject 10 with the standard time variation of occlusal force stored, in the mastication comparing section 29 and capture the occlusal habit of the subject 10 during mastication of food, it becomes feasible to correct the occlusal habit during chewing of food.

Figure 15:
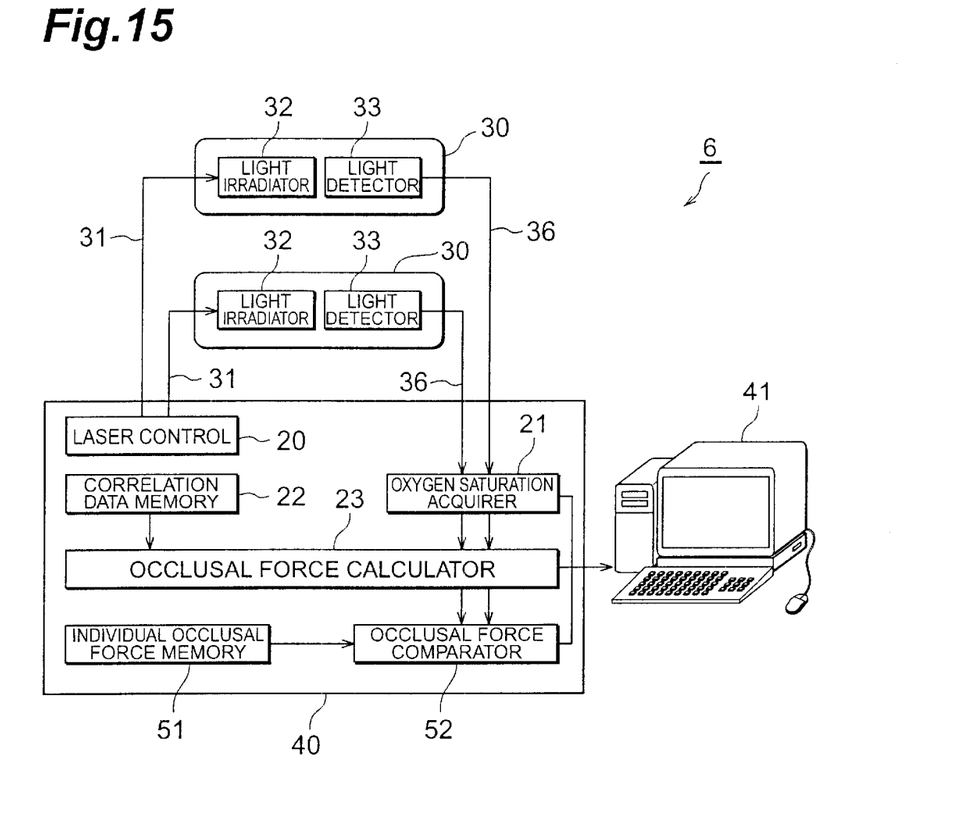
FIG. 15 is a block diagram of the occlusal force measuring apparatus of the seventh embodiment.

The seventh embodiment will be described below with reference to FIG. 15. The occlusal force measuring apparatus 6 of the present embodiment is provided with an individual occlusal force storing section 51 for storing calculated occlusal forces for every subject 10 and an occlusal force comparing section 52 for comparing a calculated occlusal force with the occlusal force of each subject 10 stored in the past, in addition to the structure of the occlusal force measuring apparatus 1 of the second embodiment, as shown in FIG. 15, and the display 41 displays data of change in occlusal force evaluated.

The operation procedures of the occlusal force measuring apparatus 6 of the present embodiment are as follows. First, occlusal forces are preliminarily calculated for every subject 10 in the procedures similar to those in the second embodiment, on the occasion of routine physical checkups or the like and are stored as a database in the individual occlusal force storing section 51. As there arises a need for occlusal adjustment thereafter, e.g., when a subject 10 puts false teeth on, the measurement of occlusal force is carried out according to the procedures similar to those in the second embodiment to calculate the current occlusal force, the occlusal force comparing section 52 compares the current occlusal force data with the past occlusal force data of that subject 10 stored in the individual occlusal force storing section 51, and the result is displayed on the display 41. A dentist or the like adjusts the occlusion, e.g., by modifying the false teeth or the like while observing the result.

Since the apparatus is provided with the individual occlusal force storing section 51 and the occlusal force comparing section 52 and configured to compare the current occlusal force of the subject 10 with the occlusal force measured in the past as described above, it allows the dentist or the like to adjust the occlusal force of the subject 10 having changed the occlusal force due to the false teeth or the like, back to the occlusal force in a normal state in the past.

The occlusal force measuring apparatus according to the present invention is not limited to the above embodiments, but can be realized in a variety of modified forms. For example, the first embodiment was adapted to stick the probes 30 to the respective skins 11 immediately above the left and right masseters of the subject 10, but, without having to be limited to this, the probes may be stuck to respective skins immediately above any other muscles used for the occlusion of teeth, e.g., the left and right temporal muscles. When the balance between the left and right occlusal forces is of little interest, the probe 30 may be mounted only on one side.

As described above, the occlusal force measuring apparatus according to the present invention is configured to irradiate the muscle used for the occlusion of teeth with the light from the light irradiating section, detect the scattered light from the muscle by the light detecting section, and acquire the oxygen saturation of this muscle, based on the scattered light thus detected. Further, the occlusal force of the subject corresponding to the oxygen saturation acquired is calculated based on the correlation data between the oxygen saturation and occlusal force, and, therefore, the present invention provides the occlusal force measuring apparatus capable of measuring the occlusal force in real time without the need for biting any detector or the like at all.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An occlusal force measuring apparatus for measuring an occlusal force of a subject, comprising:

a light irradiating section for irradiating a muscle used for occlusion of teeth of the subject, with light;

a light detecting section for detecting scattered light from said muscle upon irradiation of said muscle with the light;

an oxygen saturation acquiring section for acquiring an oxygen saturation, based on said scattered light;

a correlation data storing section prestoring correlation data between said oxygen saturation and said occlusal force; and an occlusal force calculating section for calculating said occlusal force corresponding to the oxygen saturation acquired by said oxygen saturation acquiring section, based on said correlation data stored in said correlation data storing section.

2. The occlusal force measuring apparatus according to claim 1, wherein a set of said light irradiating section and said light detecting section constitute a left scattered light acquiring section mountable on the left side of the face of the subject and another set of said light irradiating section and said light detecting section constitute a right scattered light acquiring section mountable on the right side of the face of the subject.

3. The occlusal force measuring apparatus according to claim 2, further comprising a left and right comparing section for comparing left and right occlusal forces calculated based on scattered light detected by said left scattered light acquiring section and said right scattered light acquiring section.

4. The occlusal force measuring apparatus according to claim 1, wherein said correlation data storing section stores correlation data between oxygen saturation and occlusal force for every subject and said occlusal force calculating section calculates the occlusal force, based on said correlation data for every subject.

5. The occlusal force measuring apparatus according to claim 1, further comprising a reference occlusal force storing section storing a reference occlusal force, and a clenching situation acquiring section for acquiring the number of times that said calculated occlusal force becomes not less than said reference occlusal force, hours when said calculated occlusal force becomes not less than said reference occlusal force, and occlusal forces at said hours.

6. The occlusal force measuring apparatus according to claim 1, further comprising a reference occlusal force storing section storing a reference occlusal force, and a ratio calculating section for calculating a ratio of said calculated occlusal force to said reference occlusal force.

7. The occlusal force measuring apparatus according to claim 1, further comprising a standard mastication storing section storing a time variation of occlusal force during chewing of a predetermined food, and a mastication comparing section for comparing the time variation of occlusal force during the chewing of said predetermined food with a time variation of said calculated occlusal force.

8. The occlusal force measuring apparatus according to claim 1, further comprising an individual occlusal force storing section storing said calculated occlusal force for every subject, and an occlusal force comparing section for comparing said calculated occlusal force with the occlusal force of each subject stored.

* * * * *